(12) United States Patent
Redlingshoefer et al.

(10) Patent No.: US 7,498,454 B2
(45) Date of Patent: Mar. 3, 2009

(54) PROCESS FOR PREPARING FATTY ACID ALKYL ESTERS AND ACROLEIN FROM TRIGLYCERIDES

(75) Inventors: Hubert Redlingshoefer, Muenchsteinach (DE); Christoph Weckbecker, Gruendau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 11/942,974

(22) Filed: Nov. 20, 2007

(65) Prior Publication Data

US 2008/0119663 A1    May 22, 2008

(30) Foreign Application Priority Data

Nov. 20, 2006    (DE) .................. 10 2006 054 519

(51) Int. Cl.
*C11C 1/00*    (2006.01)

(52) U.S. Cl. .................. 554/166; 554/224; 568/420; 568/435

(58) Field of Classification Search .................. None
See application file for complete search history.

(56) References Cited

FOREIGN PATENT DOCUMENTS

| DE | 42 38 493 C 1 |   | 4/1994 |
|----|---------------|---|--------|
| DE | 4238493       | * | 4/1994 |
| WO | WO 2005/021697 | * | 3/2005 |
| WO | WO 2005/021697 A1 |   | 3/2005 |

* cited by examiner

*Primary Examiner*—Deborah D Carr
(74) *Attorney, Agent, or Firm*—Oblon, Spivak, McClelland, Maier & Neustadt, P.C.

(57) ABSTRACT

A fatty acid alkyl ester of the general formula I:

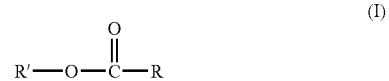

and acrolein are prepared by reacting a triglyceride of the general formula II:

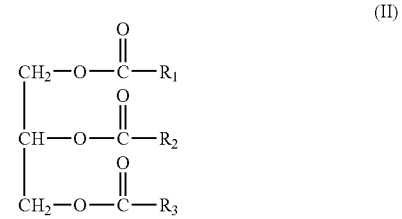

wherein a) the triglyceride is reacted using an alcohol R'—OH in the presence of a catalyst to give said fatty acid alkyl ester and glycerol; and b) the glycerol is dehydrated catalytically to acrolein, wherein R is $R_1$, $R_2$ and $R_3$, and $R_1$, $R_2$ and $R_3$ are all the same or some are the same or all are different and are each a straight-chain or branched, and optionally mono- or polyunsaturated $C_{10}$-$C_{30}$-alkyl radical, and R' is a $C_1$-$C_{10}$-alkyl radical or a $C_3$-$C_6$-cycloalkyl radical.

53 Claims, 2 Drawing Sheets

PROCESS FOR PREPARING FATTY ACID ALKYL ESTERS AND ACROLEIN FROM TRIGLYCERIDES

FIELD OF THE INVENTION

The present invention relates to a process for preparing a fatty acid alkyl ester and acrolein from a triglyceride using suitable catalysts.

DISCUSSION OF THE BACKGROUND

Triglycerides can be described, for example, by the following formula:

in which
$R_1$ to $R_3 = C_{10}$ to $C_{30}$-alkyl.

These triglycerides are, for example, an important constituent of synthetic and natural fats or vegetable oils, for example palm oil, sunflower oil, soy oil or rapeseed oil, which is used in biodiesel production. The triglycerides used in accordance with the invention may be present in contaminated form or in the form of mixtures.

Fatty acid alkyl esters or biodiesel are described in the present context by the following formula:

in which $R=R_1$ to $R_3$ and $R'=C_1$ to $C_{10}$-alkyl or $C_3$- to $C_6$-cycloalkyl.

Mixtures of these fatty acid alkyl esters are the main constituent of biodiesel. R' is preferably a $CH_3$ or $C_2H_5$ group, but usually a $CH_3$ group, since methylates in methanolic solution are usually used in biodiesel production. The transesterification of the triglycerides can also be performed with other alcohols to give corresponding fatty acid esters.

An overview of the state of use of vegetable oils and further fats for preparing biodiesel is described in G. Knothe, J. Van Gerpen, J. Krahl, The Biodiesel Handbook, OACS Verlag, 2005.

In general, the transesterification of triglycerides to fatty acid alkyl esters can be accelerated by acidic or basic catalysis. In industry, predominantly the more rapid homogeneous base catalysis is used. Preference is given to using sodium methoxide or potassium methoxide.

In the industrial production of biodiesel, important process parameters for the optimization of the yield include the concentration of the catalyst, the temperature, the residence time, the moisture content, the presence of free fatty acids and the alcohol excess (B. Freedman, E. H. Pryde, T. L. Mounts, Variables affecting the yield of fatty esters from transesterified vegetable oils, J. Am. Oil Chem. Soc., 61, 1638, 1984).

The triglycerides used contain about 10% by weight of glycerol, which is preferably isolated from the biodiesel fraction as a contaminated fraction by a phase separation or extraction after the transesterification. Both fractions are then very substantially freed of water, acids, catalysts, alcohol, salts and by-products in multistage workup steps.

Acrolein is an important intermediate and is thus of great economic significance for the preparation of acrylic acid, D,L-methionine and the methioninehydroxy analogue (MHA,=2-hydroxy-4-methylthiobutyric acid). Methionine is an essential amino acid which is used, inter alia, as a supplement in feeds. Nutrition-improving feed additives are nowadays an indispensable constituent of animal nutrition. They serve for better utilization of the food available, stimulate growth and promote protein formation. One of the most important of these additives is the essential amino acid methionine, which assumes a prominent position as a feed additive in poultry breeding in particular. In this field, so-called methionine replacements such as the methionine hydroxy analogue have, though, gained not inconsiderable significance, since they have similar growth-stimulating properties to the amino acid known for this purpose.

According to the background art, acrolein is synthesized by heterogeneously catalyzed selective oxidation of propene over mixed oxide catalysts. EP 417723 describes the synthesis of complex mixed multimetal oxide catalysts at temperatures of 300 to 380° C. and pressures of 1.4 to 2.2 bar. Ullmann's Encyclopaedia of Industrial Chemistry, 6th edition, 1999 describes the overall process including workup, in which a plurality of by-products are removed. Once the reactant mixture composed of propene, air and water has been converted at least partly over the catalyst, quenching to remove high-boiling by-products such as polymers, acrylic acid and acetic acid is effected first. In the downstream absorber, acrolein is extracted by washing. After the desorption, to recover the absorbent, the crude acrolein obtained is purified by distillation in several stages.

Scientific studies of the synthesis of acrolein from isolated glycerol are known. It is also known, for example, that glycerol can be dehydrated in the presence of acidic substances to various products.

According to Organic Synthesis I, 15-18 (1964), treatment of a mixture of pulverulent potassium hydrogensulphate, potassium sulphate and glycerol at 190 to 200° C. affords acrolein in a yield between 33 and 48%. Owing to the low yields and the high salt burdens, this process is, however, unsuitable for the industrial scale.

In the course of the studies of model substances of biomass pyrolysis oils, the catalytic treatment of glycerol over H-ZSM5 zeolites at 350 to 500° C. has also been studied—see Dao, Le H. et al. ACS Symp. Ser.: 376 (Pyrolysis Oils Biomass) 328-341 (1988). Hydrocarbons are formed only in low yields, but the formation of acrolein is pointed out.

WO 2006/092272 discloses a process for preparing acrylic acid or acrylic acid polymers by dehydrating glycerol to a dehydration product comprising acrolein, gas phase oxidation and subsequent isolation of acrylic acid and subsequent polymerization. However, a process for controlled acrolein preparation is not described.

DE 42 38 493 describes the acid-catalyzed conversion of glycerol to acrolein in the gas phase and in the liquid phase. DE 42 38 492 further relates to the synthesis of 1,2- and 1,3-propanediol by dehydrating glycerol with high yields. The glycerol used is usually in pure form or in the form of an aqueous solution.

The glycerol obtained after the phase separation in the biodiesel production is, however, generally of low value, since it is highly contaminated, for example, by excess methanol, catalyst and soaps.

To date, the above-described steps have never been combined in order to use triglycerides directly for the simultaneous preparation of fatty acid alkyl esters, especially of biodiesel and acrolein.

On the one hand, the separate preparation of biodiesel from triglycerides and acrolein from propene or glycerol gives rise to a comparatively high level of apparatus complexity and hence corresponding capital costs, since synergies in the combined preparation in an integrated system are not utilized. What also arises is corresponding logistical complexity and hence correspondingly high variable costs, for example transport and energy costs, in order to convey glycerol.

On the other hand, the disadvantage of the classical acrolein production to date, by selective oxidation from propene, is considered especially to be the complicated process in which propene has to be prepared in the gas phase and has to be isolated in the multistage workup, and also that propene is a comparatively expensive starting material whose costs are additionally increasing in a greater-than-proportional manner at the current time.

SUMMARY OF THE INVENTION

It was therefore an object of this invention to provide a process for simultaneously preparing acrolein and fatty acid alkyl esters, especially biodiesel, from triglycerides, and hence of avoiding the disadvantages of the background art.

In particular, it was an object of the invention to discover a process in which the primary transesterification of triglycerides succeeds in a simple and efficient manner with inexpensive catalysts, and the glycerol obtained as the primary product can be removed from the fatty acid alkyl ester in an efficient manner. The glycerol removed should additionally be dehydratable catalytically to acrolein substantially directly and again in a simple and efficient manner, hence avoiding the disadvantages of the background art.

It was a further object in this connection to provide very efficient, easy-to-handle catalysts which are very suitable both for the primary transesterification (biodiesel or glycerol formation) and the dehydration of the glycerol to acrolein which proceeds as the secondary reaction.

An additional object is directed to providing a process in which an aqueous acrolein solution which can be sent directly to its use, especially as a starting material for preparing methionine compounds or acrylic acid derivatives, is obtained.

This and other objects have been achieved by the present invention the first embodiment of which includes a process for preparing a fatty acid alkyl ester of the general formula I:

(I)

and acrolein by reacting a triglyceride of the general formula II:

(II)

wherein
a) said triglyceride is reacted using an alcohol R'—OH in the presence of a catalyst to give said fatty acid alkyl ester and glycerol; and
b) said glycerol is dehydrated catalytically to acrolein, wherein
R is $R_1$, $R_2$ and $R_3$, and
$R_1$, $R_2$ and $R_3$ are all the same or some are the same or all are different and are each a straight-chain or branched, and optionally mono- or polyunsaturated $C_{10}$-$C_{30}$-alkyl radical, and
R' is a $C_1$-$C_{10}$-alkyl radical or a $C_3$-$C_6$-cycloalkyl radical.

DETAILED DESCRIPTION OF THE INVENTION

The above objects and further objects which are not stated explicitly but are immediately derivable or discernible from the connections discussed herein are achieved by a process according to the present invention.

By virtue of employing a process for preparing fatty acid alkyl esters of the general formula I:

(I)

and acrolein by converting triglycerides of the general formula II:

(II)

which is characterized in that
a) the triglycerides are reacted by means of alcohols R'—OH in the presence of a suitable catalyst to give the fatty acid alkyl ester and glycerol and
b) the glycerol formed is dehydrated catalytically to acrolein, where R is $R_1$, $R_2$ and $R_3$, and $R_1$, $R_2$ and $R_3$ are all the same or some are the same or all are different and are each a straight-chain or branched and optionally mono- or polyunsaturated $C_{10}$-$C_{30}$-alkyl radical, preferably $C_{12}$-$C_{20}$-alkyl radical, and R' is a $C_1$-$C_{10}$-alkyl radical, preferably $C_1$-$C_6$-alkyl radical, a $C_3$-$C_6$-cycloalkyl radical, preferably $C_6$-cycloalkyl radical, it is possible to avoid the disadvantages of the background art which are specified above in detail.

Particular preference is given to using, in reaction step a), triglycerides in which $R_1$, $R_2$ and $R_3$ are each a $C_{12}$-$C_{18}$-alkyl radical.

Preference is additionally given to using, in reaction step a), alcohols R'—OH in which R'=methyl or ethyl. Very particular preference is given to using methanol, since the fatty acid methyl esters thus formed are most frequently used as biodiesel.

The simultaneous preparation of the two target products can be achieved by various variants of the process according to the invention. A distinction can be drawn between two main variants.

Figure 1:
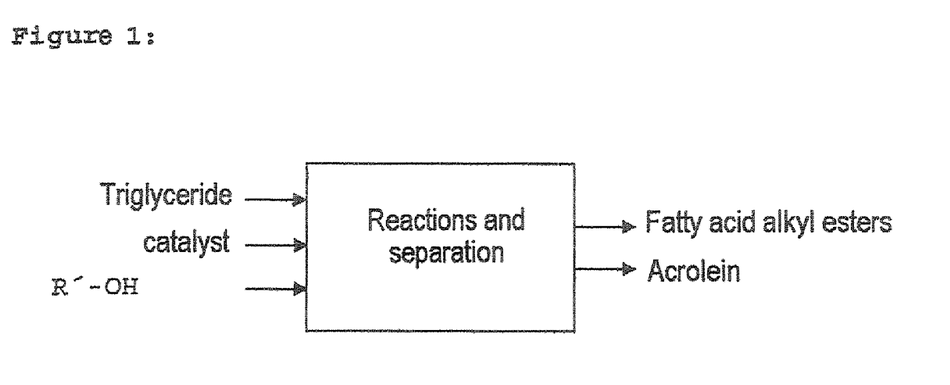
FIG. 1 shows an embodiment of the process of the present invention.

The first variant comprises a process in which reactions a) and b) are performed simultaneously in one step, i.e. in one stage, and is shown in FIG. 1.

As a result of use of a suitable catalyst or of a mixture of catalysts, the two reactions proceed in parallel. For example, a triglyceride-catalyst mixture, optionally in the presence of a solvent, is reacted with the alcohol R'OH over an acidic catalyst in the liquid phase.

For reactions a) and b), it is possible to use a homogeneous or heterogeneous acidic catalyst and/or salts of mineral acids or optionally a suitable biocatalyst. Preferably, a biocatalyst and an acid catalyst are not combined.

Preference is given to processes using a homogeneous acidic catalyst, especially a homogeneous catalyst with a pKa of <7.

Suitable catalysts are, for example, strong Brønsted acids such as sulphuric acid, phosphoric acid, toluenesulphonic acid or methanesulphonic acid.

Suitable salt-type catalysts are, for example, potassium sulphate, sodium sulphate or caesium sulphate, potassium hydrogensulphate, sodium hydrogensulphate or caesium hydrogensulphate, or mixtures of the hydrogensulphates and sulphates mentioned, lithium phosphate, iron phosphate, zinc sulphate, optionally in the homogeneous phase and optionally in the presence of a solvent.

In the case of use of a heterogeneous acidic catalyst, preference is given to those having an $H_0$ of <+2, preferably <−3.

The $H_0$ value corresponds to the Hammett acid function and can be determined by the so-called amine titration using indicators or by adsorption of a gaseous base (see Studies in surface science and catalysis, Vol. 51, 1989: "New solids and bases, their catalytic properties", K. Tanabe et al., Chapter 2, especially pages 5-9).

Chapter 1, pages 1-3 of the aforementioned document names numerous solid acids from which the person skilled in the art, if appropriate after determining the Ho value, can select the suitable catalyst.

Suitable heterogeneous catalysts are preferably zeolites, solid acids, mixed base metal oxide catalysts or acidic ion exchange resins.

Preferred heterogeneous catalysts include:

(i) natural or synthetic silicatic substances, especially mordenite, montmorillonite and acidic zeolites, especially HZSM-5, MCM-22 and zeolite beta, (ii) support materials, especially oxidic or silicatic substances, preferably aluminum oxide, titanium oxide, silicon dioxide, zirconium dioxide or mixtures thereof, coated with mono-, di- or polybasic inorganic acids, especially phosphoric acid, sulphuric acid or acidic salts of inorganic acids, (iii) oxides and mixed oxides, especially aluminum oxides, zinc oxide-aluminum oxide mixtures or heteropolyacids, or (iv) polystyrenesulphonic acid resins, especially Lewatit or Amberlite resins or perfluorinated polymeric sulphonic acid resins, especially Nafion.

Suitable biocatalysts are lipases, esterases, hydratases and/or hydrolases.

The use of a solvent is preferred, since this lowers the concentration of reactive intermediate compounds and minimizes side reactions to give oligomers, polymers and other high boilers. Moreover, the addition of an alcohol is required for the ester formation. The solvents and diluents used are known to those skilled in the art and examples include methyl tert-butyl ether, ethyl tert-butyl ether, tetrahydrofuran, 1,4-dioxane, diglyme, toluene, methyl isobutyl ketone and/or the alcohol R'—OH utilized for the transesterification. The triglycerides used may also act as solvents, as may the glycerol which is formed as an intermediate and the fatty acid alkyl esters which form and water formed in the dehydration.

The solvent is preferably added in excess and is preferably identical to the alcohol R'—OH used for the transesterification. Methanol and/or ethanol are used with very particular preference.

A reaction temperature between 30 and 500° C., preferably between 50 and 350° C., more preferably between 70 and 300° C., is employed. The pressure is adjusted such that the liquid state of the reaction mixture is maintained. Typically, the pressure is between 1 and 300 bar, preferably between 1 and 150 bar, more preferably between 1 and 50 bar. The temperature includes all values and subvalues therebetween, especially including 50, 100, 150, 200, 250, 300, 350, 400 and 450° C. The pressure includes all values and subvalues therebetween, especially including 50, 100, 150, 200 and 250 bar.

The procedure can be performed in the reaction vessels known to those skilled in the art, for example fixed bed reactors, stirred tanks, flow tubes or combinations.

Acrolein formed can be removed from the resulting reaction mixture in a known manner, alone or together with a portion of the solution or dilution medium and/or water, preferably by stripping or distillation. Unconverted intermediates or glycerol remain in the reaction stage and are converted further continually. Scavenging of the acrolein removed with water (quenching) affords an aqueous acrolein solution which can be sent directly to use or to a further purification.

According to the intended use, impurities or by-products in the acrolein can be tolerated or should be removed by workup steps. Water, acetaldehyde, formaldehyde or acetic acid and further unreactive by-products are preferably not isolated from the acrolein.

The present process variant is consequently characterized in that the acrolein formed in reaction b) is removed from the reaction mixture alone or optionally together with at least a portion of the solvent.

The acrolein can be removed from the reaction mixture by stripping, distillation, extraction, phase separation or use of membranes.

Very particular preference is given to removing the acrolein from the reaction mixture by distillation during the reaction.

For the simultaneous synthesis of acrolein and biodiesel from triglycerides, as well as the involvement of dehydration steps, selective transesterification is required. Since the dehydration to acrolein forms water which, in the fatty acid alkyl ester synthesis, can likewise lead to the undesired formation of the free fatty acid, water should preferably also be removed from the reaction mixture or equilibrium as well as glycerol, which is essentially consumed by the subsequent reaction to give acrolein. This can be effected directly in the first reaction step or in a downstream stage.

The simultaneous removal of the acrolein during the chemical reactions from the reaction mixture is possible relatively easily by means of distillation and is therefore preferred. This is caused firstly by the great differences in the boiling points of acrolein on the one hand, and triglycerides, fatty acid alkyl esters and glycerol on the other hand. The immediate removal of the acrolein formed from the reaction mixture additionally allows the yield to be increased, since acrolein in the reaction mixture is a very reactive compound which can lead to undesired side reactions. The good distillative removability of the acrolein from the reaction mixture comprising fatty acid alkyl esters becomes clear in Example 2, in which acrolein has been removed quantitatively from the biodiesel by vacuum distillation.

In a further embodiment of the invention, acrolein is not formed immediately at the start of the esterification reaction, but rather glycerol formed is removed first after the majority of the triglycerides have been converted to fatty acid alkyl esters. The glycerol formed after the transesterification is then converted to acrolein with the aid of a dehydration catalyst. The catalysts may consist of the acidic or basic components described or of components of dehydration catalysts known to those skilled in the art.

Figure 2:
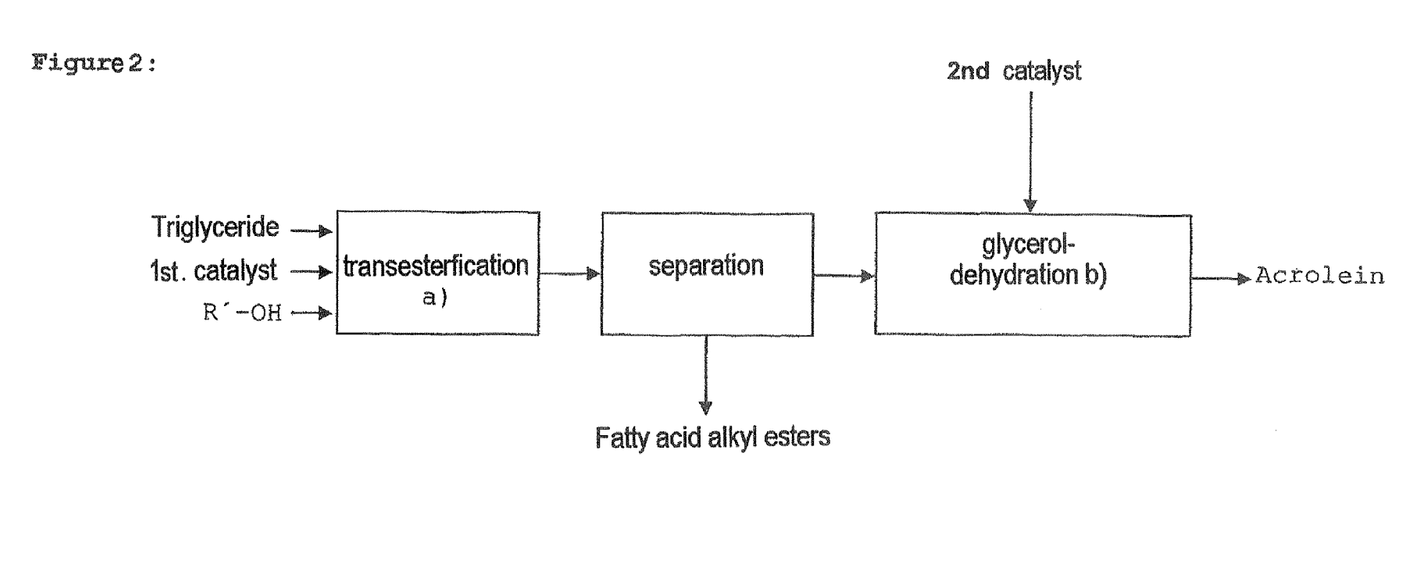
FIG. 2 shows an embodiment of the process of the present invention.

This further process variant comprises a process in which reactions a) and b) are performed in separate steps, and is shown in FIG. 2. In this process, first reaction a) (transesterification) of triglyceride with alcohol R'OH to glycerol and fatty acid alkyl esters (biodiesel) is performed in the presence of a suitable first catalyst. Subsequently, a separation into a glycerol-containing phase and a fatty acid alkyl ester-containing phase is effected. The glycerol in the glycerol-containing phase removed is dehydrated in the presence of a suitable second catalyst to acrolein (reaction b). The fatty acid alkyl ester can be used as fuel or biodiesel directly or after suitable aftertreatment, for example a substantial dewatering.

The use of the dehydration catalyst in a separate reaction step avoids the formation of reactive intermediates which can form at least from portions of the triglycerides or of the glycerol under the above-specified conditions. The reactive intermediates otherwise form undesired by-products to an increased degree, which lead to deactivation of the catalyst or to a reduction in the yield. When these intermediates are minimized, the yield of acrolein and fatty acid alkyl esters can be improved.

This can be effected firstly in a batchwise operation, in which case the dehydration catalyst, after a certain reaction time, is added to the reaction mixture which is then biphasic. For this purpose, for example, performance in a stirred tank is suitable.

Secondly, the dehydration catalyst can be fed in not until a point removed from the reactor inlet in flow direction or in a further reactor section after a phase separation has been effected. By the time the glycerol solution and the catalyst reach this point, a portion of the glycerol may already be converted to reactive intermediates. This operation can be realized industrially, for example, in a stirred tank battery or a flow tube. In this embodiment of the invention, the phase separation can be accelerated by subsequent removal of water or by distillative removal of excess alcohol, which eases the subsequent dehydration in the glycerol phase.

A further advantage of dehydration in a second step consists in the fact that the yields of acrolein and fatty acid alkyl esters can be enhanced because a temperature profile or temperature program optimized with reference to the reaction behavior of the reactants can be established separately for each step. For instance, the transesterification of the triglycerides requires a significantly lower activation energy or reaction temperature than the activation of glycerol and its first dehydration step for the rapid preparation of intermediates, for example hydroxypropionaldehyde. The fatty acid alkyl esters formed tend, in contrast, to unselective further reactions at higher temperatures of from approx. 150 to 250° C. The performance of the combined preparation of fatty acid alkyl esters and acrolein by means of passage through two reaction stages under different reaction conditions thus constitutes a preferred embodiment.

A preferred embodiment of the process is characterized in that reaction a) is performed with the aid of an alkaline catalyst for which the pKa of the corresponding acid is >13.

Mention should be made in particular of alkali metal alkoxides of the alcohol R'OH used for the transesterification. Preference is given to the alkali metal alkoxides of the $C_1$-$C_4$-alcohols, especially alkali metal methoxides or ethoxides and most preferably sodium methoxide.

The possibility of using alkaline catalysts for the transesterification in reaction a) constitutes an additional advantage in the second process variant, because the subsequent removal of the glycerol phase here results in virtually no reaction taking place with the acidic catalysts to be used in the dehydration.

Just like in the case of reaction in one step, it is also possible here that reaction a) is performed with the aid of a homogeneous or heterogeneous acidic catalyst. This catalyst may additionally be different from the acidic catalyst to be used in the dehydration, which further increases the variability and flexibility of the process.

In the case of use of a homogeneous acidic catalyst in reaction a), preference is given to using catalysts with a pKa of <7.

In the case of use of a heterogeneous acidic catalyst in reaction a), preference is given to using catalysts with an $H_0$ of <+2, preferably <−3.

Both the alkali- and the acid-catalyzed transesterification a) is performed at temperatures of 20 to 150° C., preferably 25 to 100° C., preferentially of 25 to 80° C. The temperature includes all values and subvalues therebetween, especially including 40, 50, 60, 70, 80, 90, 100, 110, 120, 130 and 140° C.

In this way, it is possible, through selection of optimal reaction conditions, to form glycerol as well as biodiesel in a first reaction stage and then to convert it selectively to acrolein in a second stage.

According to the invention, it is also possible that reaction a) is performed with the aid of a biocatalyst.

The biocatalysts used are preferably lipases, esterases, hydratases or hydrolases.

In the process variant with separate reaction steps a) and b), the glycerol formed as the primary product is removed completely or partly from the reaction mixture of reaction a), and dehydrated catalytically in the reaction b) proceeding separately to acrolein.

For the dehydration reaction b), it is possible in accordance with the invention to use a homogeneous or heterogeneous acidic catalyst.

In the case of homogeneous catalysts, preference is given to those having a pKa of <7.

In particular, it is possible here to use sulphuric acid, phosphoric acid, toluenesulphonic acid or methanesulphonic acid as the catalyst.

Furthermore, the homogeneous catalysts used for the dehydration reaction b) are preferably salts of mineral acids, optionally in the presence of a solvent.

Very particular preference is given to using potassium sulphate, sodium sulphate or caesium sulphate, potassium hydrogensulphate, sodium hydrogensulphate or caesium hydrogensulphate, or mixtures of the hydrogensulphates and sulphates mentioned, lithium phosphate, iron phosphate, zinc sulphate, optionally in the presence of a solvent, as a catalyst.

In the case of heterogeneous catalysts, preference is given to those having an $H_0$ of <+2, preferably <−3.

Preference is given to using zeolites, solid acids, mixed base metal oxide catalysts or acidic ion exchange resins as the heterogeneous catalyst.

Suitable heterogeneous catalysts include in particular:

(i) natural or synthetic silicatic substances, especially mordenite, montmorillonite and acidic zeolites, especially HZSM-5, MCM-22 and zeolite beta, (ii) support materials, especially oxidic or silicatic substances, preferably aluminum oxide, titanium dioxide, silicon dioxide, zirconium dioxide or mixtures thereof, coated with mono-, di- or polybasic inorganic acids, especially phosphoric acid, sulphuric acid or acidic salts of inorganic acids, (iii) oxides and mixed oxides, especially aluminum oxides, zinc oxide-aluminum oxide mixtures or heteropolyacids, or (iv) polystyrenesulphonic acid resins, especially Lewatit or Amberlite resins or perfluorinated polymeric sulphonic acid resins, especially Nafion.

The reaction conditions to be established with preference correspond to those which are employed in the above-described first one-stage process variant. Only the reaction temperature of the second reaction, of the dehydration b), compared to the first reaction, the transesterification a), is at higher temperatures of 50 to 400° C., preferably 100 to 350° C. The temperature includes all values and subvalues therebetween, especially including 100, 150, 200, 250, 300 and 350° C.

Preference is equally given to performing the dehydration reaction b) with the aid of a biocatalyst.

The biocatalysts used are, for example, dehydratases, hydratases or hydrolases.

The reaction step b) is performed preferably in the presence of a solvent.

Preferred solvents are methyl tert-butyl ether, ethyl tert-butyl ether, tetrahydrofuran, 1,4-dioxane, diglyme, toluene, methyl isobutyl ketone and/or the alcohol R'—OH already utilized in reaction step a).

One possibility is that the glycerol is removed from the reaction mixture a) by distillation.

The glycerol can be removed in a distillation column attached to the first reaction apparatus by a vacuum distillation of reaction mixture a).

A particularly advantageous embodiment of the process consists in removing glycerol from the reaction mixture a) by reactive distillation and, at the same time, dehydrating it to acrolein over the simultaneously present acidic catalyst (reaction step b)).

In this case, a heterogeneous dehydration catalyst, preferably of the type (i) to (iv) described in detail above, which simultaneously accelerates the conversion of the glycerol to be removed to acrolein, is present in the distillation column. The temperature in the down-stream column is between 50 and 300° C., preferably between 80 and 250° C., more preferably between 100 and 200° C. The pressure there is between 0.1 and 1500 mbar, preferably between 0.5 and 1000 mbar, more preferably between 2 and 100 mbar.

The solid, generally insoluble acidic dehydration catalyst is installed within the distillation column as a bed or as a coating.

The advantage of performing reactions a) and b) in two separate steps also consists in the fact that the stability of the process is improved owing to delimited process steps in continuous operation.

In addition to distillation or reactive distillation, it is also possible to use further means of removing the glycerol.

A further preferred embodiment of the process according to the invention is characterized in that glycerol is removed from the reaction solution by simple phase separation after a lipophilic phase A comprising fatty acid alkyl esters and a glycerol-containing hydrophilic phase B have formed.

This phase separation can additionally be enabled or promoted by adding a phase separator.

Preferred phase separators are water and/or an organic solvent and/or fatty acid alkyl esters.

The combined preparation of acrolein and fatty acid alkyl esters can also be achieved in accordance with the invention by deliberately promoting the phase separation into a lipophilic phase A comprising triglyceride and fatty acid alkyl esters and into a water- and glycerol-containing hydrophilic phase B actually at the start of the transesterification, and by virtue of reactions a) and b) proceeding in parallel in the two different liquid phases (biphasic catalysis). This can be effected firstly by the addition of water or other solvents.

On the other hand, the excess alcohol used for the transesterification can be removed by distillation in order to accelerate the phase separation. This has the advantage that catalysts optimized in each case can be used for the transesterification reaction a) and for the dehydration reaction b). The two reactions additionally proceed separately in the particular phases without influencing one another.

Preference is therefore given to a process in which reaction a) is performed in the lipophilic phase A, which comprises triglyceride and fatty acid alkyl esters, and reaction b) in the hydrophilic phase B which comprises glycerol, water and acrolein.

The easy transfer of the acrolein from the lipophilic phase A comprising fatty acid alkyl esters to the aqueous hydrophilic phase B becomes clear in Example 1, in which acrolein is found predominantly in the aqueous phase.

The yield of the two target products can thus be enhanced overall by virtue of fewer unselective side reactions proceeding. It is also desired to bind residual moisture or added water exclusively in the glycerol phase, since it otherwise leads to an enhanced degree of undesired formation of free fatty acids.

The catalyst systems for the transesterification and for the dehydration are, in the case of biphasic catalysis, adjusted such that, in the case of use of homogeneous catalysts, the transesterification catalyst dissolves in the triglyceride phase and the dehydration catalyst in the glycerol-containing phase and not vice versa, so that a catalyst preferably soluble in the lipophilic phase A accelerates reaction a) there, and a catalyst preferably in the hydrophilic phase B accelerates reaction b) there.

In general, a homogeneous solution is advantageous for good mass transfer, but is not absolutely necessary here. This is even exploited deliberately by the principle of biphasic catalysis, where the acrolein product is readily soluble in the aqueous glycerol phase. Acrolein can thus be separated from the fatty acid alkyl ester in a simple manner by phase separation or additional extraction without complicated workup, and the overall process can thus be simplified. This also becomes clear in Example 1.

The ester cleavage is an equilibrium reaction which can be directed in one or another direction according to the reaction conditions. This is exploited deliberately in the embodiment of biphasic catalysis described by removing glycerol as the reaction product from the phase comprising triglyceride and fatty acid alkyl ester and hence from the equilibrium. Reaction a) is thus accelerated to an enhanced degree in the direction of fatty acid alkyl ester or biodiesel, and a back-reaction to triglycerides is minimized. As a result, reaction conditions which would otherwise not be optimal for the production of biodiesel can be established, or the range of suitable reaction conditions can be widened. For example, the excess of alcohol can be lowered.

Fatty acid alkyl esters of the formula I are preferably obtained from the lipophilic phase A and can be used as a fuel directly or optionally after further purification.

Acrolein is obtained from the hydrophilic phase B and can be used as a starting material for methionine products or acrylic acid directly or optionally after further purification.

A further embodiment of the invention is characterized in that the triglycerides used are converted catalytically to fatty acid alkyl esters and acrolein in the presence of alcohol R'OH, the transesterification reaction a) and the dehydration reaction b) being performed simultaneously or spatially separately using membranes (membrane separation). The membrane selectively retains the triglycerides and fatty acid alkyl esters (retentate), while glycerol formed passes into the permeate. As a result, the separation is effected without a separate workup step, which lowers the preparation costs.

For instance, glycerol can, in accordance with the invention, also be removed by membrane filtration from the reaction mixture of reaction a). Suitable membrane materials are especially organic or ceramic materials.

The dehydration reaction can also be effected by means of suitable catalysts immobilized on or in the membrane or by means of a separate catalyst addition into the permeate. The catalytically active components for the dehydration may also be an insoluble constituent of the membrane.

Suitable membranes are, for example, solubility membranes or diffusion membranes from micro- or ultrafiltration, which, owing to their functional groups, polarity or pore structure, retain the triglycerides, but are permeable to glycerol. Suitable membranes are especially formed from organic materials such as polyether sulphones (PES), cellulose esters, polyimides or polyether imides, poly(fatty acid amides) or polyacrylonitrile (PAN), or from ceramic materials such as aluminum oxide, titanium dioxide, silicon dioxide, zirconium dioxide (baddeleyite) and combinations thereof.

The advantages of the simultaneous preparation of biodiesel and acrolein described consist in increased productivity, addition of value and saving of time. At the same time, the transport and energy costs are reduced. Overall, the production of biodiesel and acrolein becomes more economically viable.

At the same time, relatively high-boiling by-products which are obtained in the acrolein synthesis can be added to the biodiesel as additional calorific value or, if appropriate, be left in the biodiesel. These may, for example, be dimers or trimers of acrolein or ethers of glycerol.

The invention also provides a mixture which comprises acrolein and has been prepared by the process according to the invention detailed here, and a mixture which comprises fatty acid alkyl esters of the formula I and has been prepared by the process according to the invention detailed here.

The examples which follow are intended to illustrate the invention described in detail, but in no way to have any restrictive effect.

EXAMPLES

Example 1

50 g of biodiesel and 50 g of acrolein were mixed and formed a homogeneous mixture. In a separating funnel, this homogeneous mixture was admixed with 250 g of water, shaken and left to stand, in the course of which two phases formed. After the formation of the phase interface, the lower aqueous phase in the separating funnel was removed and analyzed by means of gas chromatography to determine the acrolein content. Overall, 33.4 g of acrolein were obtained in the aqueous phase in this way. Even in the case of simple single-stage extraction with water, it was thus possible to remove a large portion of the acrolein from the biodiesel.

Example 2

The flask of a rotary evaporator was initially charged with a mixture of 50 g of biodiesel and 50 g of acrolein and heated to 35° C. in a water bath. By means of a water-jet pump, the mixture was placed under vacuum slowly. In the cooled distillation receiver, 50 mg of hydroquinone were initially charged to stabilize the acrolein distilled. Within one hour, a distillate of 49.1 g of acrolein was obtained. The purity of the distillate was confirmed to be at least 99.5% by means of gas chromatography. 50.6 g remained in the flask of the rotary evaporator.

German patent application 10 2006 054 519.2 filed Nov. 20, 2006, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:
1. A process for preparing a fatty acid alkyl ester of the general formula I:

and acrolein by reacting a triglyceride of the general formula II:

wherein
a) said triglyceride is reacted using an alcohol R'—OH in the presence of a catalyst to give said fatty acid alkyl ester and glycerol; and
b) said glycerol is dehydrated catalytically to acrolein,
wherein
R is $R_1$, $R_2$ and $R_3$, and
$R_1$, $R_2$ and $R_3$ are all the same or some are the same or all are different and are each a straight-chain or branched, and optionally mono- or polyunsaturated $C_{10}$-$C_{30}$-alkyl radical, and R' is a $C_1$-$C_{10}$-alkyl radical or a $C_3$-$C_6$-cycloalkyl radical.

2. The process according to claim 1, wherein $R_1$, $R_2$ and $R_3$ are a $C_{12}$-$C_{18}$-alkyl radical.

3. The process according to claim 1, wherein R'=methyl or ethyl.

4. The process according to claim 1, wherein reactions a) and b) are performed simultaneously in one step.

5. The process according to claim 1, wherein said catalyst for reactions a) and b) is independently selected from the group consisting of a homogeneous acidic catalyst, a heterogeneous acidic catalyst, a salt of a mineral acid, combinations thereof and a biocatalyst.

6. The process according to claim 5, wherein a homogeneous catalyst with a pKa of <7 is used.

7. The process according to claim 6, wherein said catalyst is sulphuric acid, phosphoric acid, toluenesulphonic acid or methanesulphonic acid.

8. The process according to claim 5, wherein said catalyst is potassium sulphate, sodium sulphate, caesium sulphate, potassium hydrogensulphate, sodium hydrogensulphate, caesium hydrogensulphate, mixtures of the hydrogensulphates and sulphates mentioned, lithium phosphate, iron phosphate, or zinc sulphate,
wherein said catalyst is optionally used in the presence of a solvent.

9. The process according to claim 5, wherein said catalyst is a heterogeneous catalyst with an $H_0$ value of <+2.

10. The process according to claim 9, wherein said catalyst is a zeolite, a solid acid, a mixed base metal oxide catalyst or acidic ion exchange resin.

11. The process according to claim 10, wherein said catalyst is
(i) a natural or synthetic silicatic substance,
(ii) a support material coated with mono-, di- or polybasic inorganic acids,
(iii) an oxide, a mixed oxide or combinations thereof, or
(iv) a polystyrenesulphonic acid resin, perfluorinated polymeric sulphonic acid resins or mixtures thereof.

12. The process according to claim 5, wherein said biocatalyst is a lipase, an esterase, a hydratase, a hydrolase or mixtures thereof.

13. The process according to claim 1, which is performed in the presence of a solvent.

14. The process according to claim 13, wherein the solvent is methyl tert-butyl ether, ethyl tert-butyl ether, tetrahydrofuran, 1,4-dioxane, diglyme, toluene, methyl isobutyl ketone, the alcohol R'—OH utilized for the transesterification in reaction a) or mixtures thereof.

15. The process according to claim 13, wherein the acrolein formed in reaction b) is removed from the reaction mixture alone or optionally together with at least a portion of the solvent.

16. The process according to claim 15, wherein the acrolein is removed from the reaction mixture by stripping, distillation, extraction, phase separation or use of membranes.

17. The process according to claim 16, wherein the acrolein is removed from the reaction mixture by distillation during the reaction.

18. The process according to claim 1, wherein reactions a) and b) are performed in separate steps.

19. The process according to claim 18, wherein reaction a) is performed with the aid of an alkaline catalyst for which the pKa of the corresponding acid is >13.

20. The process according to claim 19, wherein the alkaline catalyst is an alkali metal alkoxide of the alcohol R'—OH used for the transesterification or an alkali metal methoxide or ethoxide.

21. The process according to claim 1, wherein reaction a) is performed with the aid of a homogeneous or heterogeneous acidic catalyst.

22. The process according to claim 21, wherein a homogeneous acidic catalyst with a pKa of <7 is used.

23. The process according to claim 21, wherein a heterogeneous catalyst with an $H_0$ of <+2 is used.

24. The process according to claim 18, wherein reaction a) is performed with the aid of a biocatalyst.

25. The process according to claim 24, wherein a lipase, esterase, hydratase or hydrolase is used as the biocatalyst.

26. The process according to claim 18, wherein the glycerol formed as the primary product from the reaction mixture of reaction a) is removed completely or partly and is dehydrated catalytically to acrolein in reaction b).

27. The process according to claim 26, wherein a homogeneous or heterogeneous acidic catalyst is used for the dehydration reaction b).

28. The process according to claim 27, wherein a homogeneous catalyst with a pKa of <7 is used.

29. The process according to claim 28, wherein sulphuric acid, phosphoric acid, toluenesulphonic acid or methanesulphonic acid is used as the catalyst.

30. The process according to claim 26, wherein salts of mineral acids are used as catalysts for the dehydration reaction b).

31. Process according to claim 30, wherein said catalyst is potassium sulphate, sodium sulphate, caesium sulphate, potassium hydrogensulphate, sodium hydrogensulphate, caesium hydrogensulphate, mixtures of the hydrogensulphates and sulphates mentioned, lithium phosphate, iron phosphate, or zinc sulphate,
wherein said catalyst is optionally used in the presence of a solvent.

32. The process according to claim 26, wherein a heterogeneous catalyst with an $H_0$ of <+2 is used for the dehydration reaction b).

33. The process according to claim 32, wherein said catalyst is a zeolite, a solid acid, a mixed base metal oxide catalyst or acidic ion exchange resin.

34. The process according to claim 33, wherein said catalyst is
(i) a natural or synthetic silicatic substance,
(ii) a support material coated with mono-, di- or polybasic inorganic acids,
(iii) an oxide, a mixed oxide or combinations thereof, or
(iv) a polystyrenesulphonic acid resin, perfluorinated polymeric sulphonic acid resins or mixtures thereof.

35. The process according to claim 26, wherein the dehydration reaction b) is performed with a biocatalyst.

36. The process according to claim 35, wherein a dehydratase, hydratase or hydrolase is used as the biocatalyst.

37. The process according to claim 26, wherein reaction b) is performed in the presence of a solvent.

38. The process according to claim 37, wherein the solvent is methyl tert-butyl ether, ethyl tert-butyl ether, tetrahydrofuran, 1,4-dioxane, diglyme, toluene, methyl isobutyl ketone, the alcohol R'—OH utilized for the transesterification in reaction a) or mixtures thereof.

39. The process according to claim 26, wherein glycerol is removed from the reaction mixture of step a) by distillation.

40. The process according to claim 39, wherein glycerol is removed from the reaction mixture by reactive distillation and, at the same time, is dehydrated to acrolein over an acidic catalyst present simultaneously.

41. The process according to claim 26, wherein glycerol is removed from the reaction solution by membrane filtration.

42. The process according to claim 41, wherein the membranes used are organic or ceramic materials.

43. The process according to claim 26, wherein glycerol is removed from the reaction solution by phase separation after a lipophilic phase A comprising fatty acid alkyl esters and a glycerol-containing hydrophilic phase B have formed.

44. The process according to claim 43, wherein the phase separation is initiated or promoted by addition of a phase separation agent.

45. The process according to claim 44, wherein the phase separation agent is selected from the group consisting of water, an organic solvent, a fatty acid alkyl ester and mixtures thereof.

46. The process according to claim 18, wherein reactions a) and b) proceed in parallel in two different liquid phases.

47. The process according to claim 46, wherein reaction a) is performed in a lipophilic phase A which comprises triglyceride and fatty acid alkyl esters.

48. The process according to claim 47, wherein a catalyst which is soluble in the lipophilic phase A accelerates the reaction a) there.

49. The process according to claim 47, wherein reaction b) is performed in a hydrophilic phase B which comprises glycerol, water and acrolein.

50. The process according to claim 49, wherein a catalyst which is soluble in the hydrophilic phase B accelerates the reaction b) there.

51. The process according to claim 46, wherein the fatty acid alkyl esters of the formula I are obtained from the phase A.

52. The process according to claim 46, wherein acrolein is obtained from the phase B.

53. An acrolein-comprising mixture, comprising:
said fatty acid alkyl esters of the formula I; and
said acrolein;
wherein said mixture is prepared by the process according to claim 1.

\* \* \* \* \*